United States Patent
Parsonage et al.

(10) Patent No.: US 8,133,250 B2
(45) Date of Patent: Mar. 13, 2012

(54) MEDICAL DEVICES COMPRISING NANOCOMPOSITES

(75) Inventors: Edward Parsonage, St. Paul, MN (US); Daniel J. Horn, Shoreview, MN (US); John J. Chen, Plymouth, MN (US); Paul J. Miller, St. Paul, MN (US); Douglas A. Devens, Jr., St. Paul, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/563,780

(22) Filed: Sep. 21, 2009

(65) Prior Publication Data

US 2010/0010440 A1   Jan. 14, 2010

Related U.S. Application Data

(63) Continuation of application No. 10/259,545, filed on Sep. 27, 2002, now Pat. No. 7,591,831.

(60) Provisional application No. 60/331,332, filed on Sep. 28, 2001, provisional application No. 60/327,629, filed on Oct. 5, 2001.

(51) Int. Cl.
*A61M 25/00* (2006.01)
*A61M 25/10* (2006.01)

(52) U.S. Cl. ........ 606/194; 606/200; 524/262; 524/267; 524/269; 524/445; 524/496

(58) Field of Classification Search .......... 606/194–198, 606/108; 604/96.01
See application file for complete search history.

(56) References Cited

U.S. PATENT DOCUMENTS

| | | | |
|---|---|---|---|
| 4,762,129 A | 8/1988 | Bonzel | |
| 4,950,227 A | 8/1990 | Savin et al. | |
| 5,021,515 A | 6/1991 | Cochran et al. | |
| 5,034,252 A | 7/1991 | Nilsson et al. | |
| 5,040,548 A | 8/1991 | Yock | |
| 5,156,594 A | 10/1992 | Keith | |
| 5,195,969 A | 3/1993 | Wang et al. | |
| 5,350,395 A | 9/1994 | Yock | |
| 5,451,233 A | 9/1995 | Yock | |
| 5,534,007 A | 7/1996 | St. Germain et al. | |
| 5,538,510 A | 7/1996 | Fontirroche et al. | |
| 5,554,670 A | 9/1996 | Giannelis et al. | |
| 5,747,560 A | 5/1998 | Christiani et al. | |

(Continued)

FOREIGN PATENT DOCUMENTS

EP   1 388 346 A1   11/2004

(Continued)

OTHER PUBLICATIONS

Bins et al., "Nanocomposite Market Opportunities," © 2001 Bins & Associates, 8 sheets.

(Continued)

*Primary Examiner* — Elizabeth Houston
(74) *Attorney, Agent, or Firm* — Seager, Tufte & Wickhem LLC

(57) ABSTRACT

The present invention provides medical devices comprising nanocomposite materials. By utilizing nanocomposites in the production thereof, the inventive medical devices can be produced with various advantageous properties. Methods of producing the inventive medical devices are also provided. Inasmuch as the inventive devices are expected to provide certain advantages in their use, there is also provided a method of medical care including methods of treatment or diagnosis, wherein the inventive devices are brought into therapeutic contact with a body to be treated or diagnosed thereby.

12 Claims, 1 Drawing Sheet

U.S. PATENT DOCUMENTS

| | | | |
|---|---|---|---|
| 5,749,888 A | 5/1998 | Yock | |
| 5,797,877 A | 8/1998 | Hamilton et al. | |
| 5,811,447 A | 9/1998 | Kunz et al. | |
| 5,836,926 A | 11/1998 | Peterson et al. | |
| 5,843,032 A | 12/1998 | Kastenhofer | |
| 5,853,886 A | 12/1998 | Pinnavaia et al. | |
| 5,948,483 A | 9/1999 | Kim et al. | |
| 5,980,486 A | 11/1999 | Enger | |
| 6,001,118 A | 12/1999 | Daniel et al. | |
| 6,010,521 A | 1/2000 | Lee et al. | |
| 6,016,848 A | 1/2000 | Egres, Jr. | |
| 6,093,463 A | 7/2000 | Thakrar | |
| 6,126,740 A | 10/2000 | Schulz et al. | |
| 6,129,708 A | 10/2000 | Enger | |
| 6,129,739 A | 10/2000 | Khosravi | |
| 6,156,350 A | 12/2000 | Constantz | |
| 6,228,471 B1 | 5/2001 | Neerinck et al. | |
| 6,245,849 B1 | 6/2001 | Morales et al. | |
| 6,252,020 B1 | 6/2001 | Kuo et al. | |
| 6,331,262 B1 | 12/2001 | Haddon et al. | |
| 6,331,265 B1 | 12/2001 | Dupire et al. | |
| 6,336,934 B1 | 1/2002 | Gilson et al. | |
| 6,350,805 B1 | 2/2002 | Korbee et al. | |
| 6,368,569 B1 | 4/2002 | Haddon et al. | |
| 6,414,086 B1 | 7/2002 | Wang et al. | |
| 6,417,262 B1 | 7/2002 | Turner et al. | |
| 6,447,439 B1 | 9/2002 | Vallana et al. | |
| 6,520,952 B1 | 2/2003 | Jimenez | |
| 6,569,932 B2 | 5/2003 | Hsiao et al. | |
| 6,586,548 B2 | 7/2003 | Bonafini, Jr. et al. | |
| 6,653,365 B2 | 11/2003 | Jia | |
| 6,716,919 B2 | 4/2004 | Lichtenhan et al. | |
| 6,737,447 B1 | 5/2004 | Smith et al. | |
| 6,740,191 B2 | 5/2004 | Clarke et al. | |
| 6,793,994 B2 | 9/2004 | Tsai et al. | |
| 6,833,392 B1 | 12/2004 | Acquarulo, Jr. et al. | |
| 6,905,511 B2 | 6/2005 | Wang et al. | |
| 7,517,353 B2 | 4/2009 | Weber | |
| 2001/0009769 A1 | 7/2001 | Williams et al. | |
| 2002/0011030 A1 | 1/2002 | Williams et al. | |
| 2002/0014182 A1 | 2/2002 | Yadav et al. | |
| 2002/0022678 A1 | 2/2002 | Lan et al. | |
| 2002/0049495 A1 | 4/2002 | Kutryk et al. | |
| 2002/0086896 A1 | 7/2002 | Kunz et al. | |
| 2002/0137834 A1 | 9/2002 | Barbee et al. | |
| 2003/0093107 A1 | 5/2003 | Parsonage et al. | |

FOREIGN PATENT DOCUMENTS

| | | |
|---|---|---|
| GB | 2 285 401 A | 12/1995 |
| JP | 2000-325464 A | 11/2000 |
| JP | 2001-129075 A | 5/2001 |
| JP | 2003-533276 A | 11/2003 |
| JP | 2005-503865 A | 2/2005 |
| WO | 93/11190 A1 | 6/1993 |
| WO | 96/18686 A1 | 6/1996 |
| WO | 98/30604 A1 | 7/1998 |
| WO | 99/38914 A3 | 8/1999 |
| WO | 99/41299 A1 | 8/1999 |
| WO | 00/57932 A2 | 10/2000 |
| WO | 01/30864 A2 | 5/2001 |
| WO | 01/34685 A1 | 5/2001 |
| WO | 01/48080 A1 | 7/2001 |
| WO | 01/68158 A1 | 9/2001 |
| WO | 01/87193 A1 | 11/2001 |

OTHER PUBLICATIONS

Product Information Pamphlet, "Carbon Nanotube Technology," CSIRO, Division of Molecular Science, Victoria, Australia, date unknown, 2 sheets.

Bandyopadhyaya, Rajidip et al., "Stabilization of Individual Carbon Nanotubes in Aqueous Solutions," Nano Letters vol. 2, No. 1 (2002) pp. 25-28.

Dzenis, Yuris et al., "Continuous Carbon Nanofibers for Nanofiber Composites," Materials Research Society Symp. Proc., vol. 702 (2002) pp. U5.4.1-U5.4.6.

Dagani, Ron et al., "Sugary Ways to Make Nanotubes Dissolve," Science & Technology, vol. 80, No. 28, Jul. 15, 2002, pp. 38-39.

Manias, E., "Origins of the Materials Properties Enhancements in Polymer/Clay Nanocomposites," Nanocomposites 2001, Delivering New Value to Plastics, Jun. 25-27, 2001, Chicago, IL, ECM Publishers, IL 2001, pp. 1-11.

O'Connell, Michael J. et al., "Reversible Water-Solubilization of Single-Walled Carbon Nanotubes by Polymer Wrapping," Chemical Physics Letters, 342 (2001) pp. 265-271.

Pompeo, Francisco et al., "Water Solubilization of Single-Walled Carbon Nanotubes by Functionalization with Glucosamine," Nano Letters, vol. 2, No. 4 (2002) pp. 369-373.

Ramírez, C., et al., "Selection of a Precursor of a Monofunctioinal Polyhedral Oligomeric Silsesquioxane Reacted with Aromatic Diamines," Journal of Applied Polymer Science, vol. 92, No. 3, May 5, 2004, pp. 1576-1583.

Schwab, Joseph J. et al., "Polyhedral Oligomeric Silsesquioxane (POSS)-Based Polymers," Applied Organometallic Chemistry, vol. 12, No. 10-11, Oct.-Nov. 1998, pp. 707-713.

Star, Alexander et al., "Starched Carbon Nanotubes," Angew. Chem. Int. Ed., 2002, 41, No. 14, pp. 2508-2512.

Wilson, Dr. Phillip S., "Nano-Composite Market Opportunities," Inspired Innovations, L.L.C., date unknown, 9 sheets.

Brandhorst, Henry et al., "POSS® Coatings as Replacements for Solar Cell cover Glasses," 4th International Energy Conversion Engineering Conference and Exhibit (IECEC), Jun. 26-29, 2006, San Diego, CA © 2006 AIAA, 4 sheets.

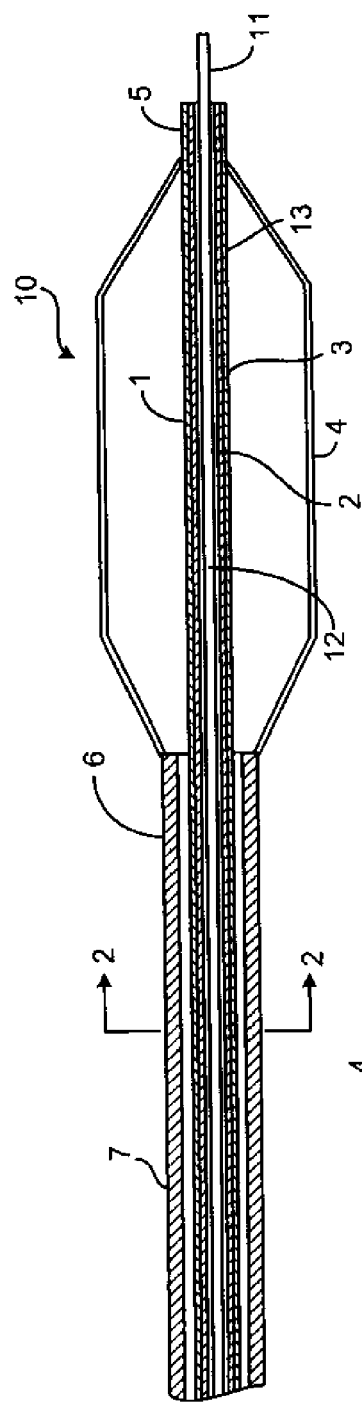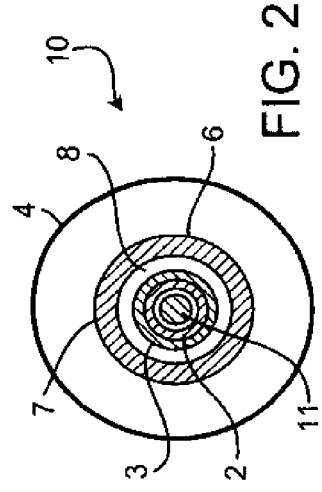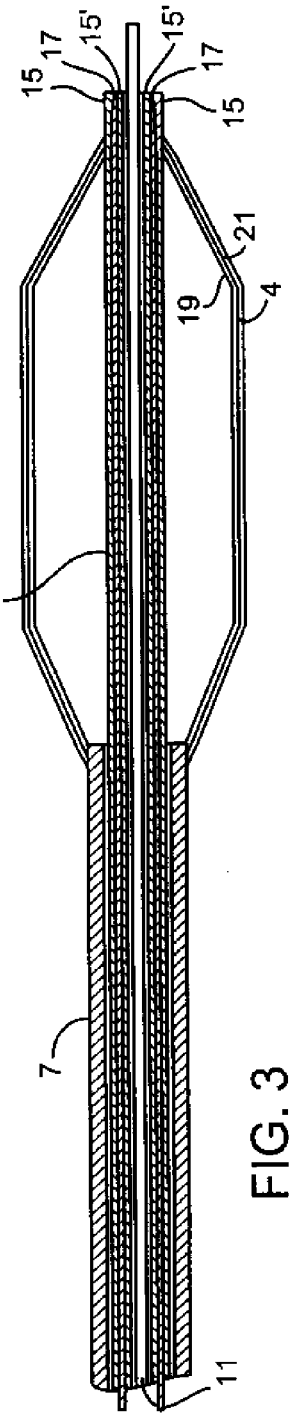

MEDICAL DEVICES COMPRISING NANOCOMPOSITES

CROSS REFERENCE TO RELATED APPLICATIONS

This application is a continuation of co-pending U.S. application Ser. No. 10/259,545, filed Sep. 27, 2002, which claims the benefit of priority of U.S. Provisional Patent Application Ser. No. 60/331,332, filed Sep. 28, 2001, and U.S. Provisional Patent Application Ser. No. 60/327,629 filed Oct. 5, 2001, the entire disclosures of which are all hereby incorporated herein by reference.

FIELD OF THE INVENTION

The present invention relates to medical devices including one or more components comprised of one or more nanocomposite materials. By utilizing nanocomposites in the manufacture of the inventive medical devices, certain properties of the nanocomposites may be exploited in ways particularly advantageous in the medical device industry.

BACKGROUND OF THE INVENTION

The medical device industry is but one example of an industry where the products or devices produced and used therein requires the products to exhibit a diverse array of properties. Transluminal medical devices are one example. Such devices are typically introduced into the vasculature of a patient at a point remote from the treatment site, a procedure that can be uncomfortable for the patient. In order to perform acceptably, and to minimize the trauma to the patient, transluminal devices typically exhibit diverse, and at times divergent, performance characteristics. For example, many such devices desirably exhibit good maneuverability so as to be manipulated to and/or inserted at a location requiring treatment, but yet sufficiently strong in the longitudinal direction so as not to buckle or kink when being so manipulated. In fact, many medical devices require a combination of these, and other, properties such as strength, thermal stability, structural stability, flexibility, opacity, radio-opacity, storage stability, lubricity, stability to sterilization treatment, etc., in order to be effective for their intended purpose.

Material selection is thus very important to the therapeutic efficacy of many medical devices since the properties of the materials used often dictate the properties of the overall device. However, the range of properties available from one, or even a combination of, material(s) is often not as broad as would be desired in medical device applications. As a result, many medical devices need to be manufactured from a combination of materials, processed in a specific manner, coated, or subjected to other treatments, in order to exhibit the desired and/or required characteristics.

Thus, there is a continuing need in the medical device industry to develop or discover additional materials that exhibit the range of properties required for a medical device.

SUMMARY OF THE INVENTION

The present invention provides medical devices comprising nanocomposite materials. According to the invention, utilization of nanocomposites for medical devices can provide the devices with many, or all, of the diverse properties often desirable in the same. That is, inasmuch as such devices often desirably exhibit a vast number of oftentimes divergent properties, it can be difficult to manufacture such devices without utilizing an extensive number of materials and processing techniques. By employing the present invention, however, medical devices can be produced with a desired array of properties using a lesser amount of materials and/or processing techniques, or medical devices can be produced wherein one or more of the properties are enhanced.

As a result, the present invention provides a medical device comprising at least one nanocomposite material. The nanocomposite material(s) may desirably be employed to produce one or more components of the device, or may be utilized to produce the device in total. The nanocomposite is desirably comprised of a matrix material and at least one plurality of filler particles. In some embodiments, the nanocomposite may comprise a matrix including a first plurality of filler particles comprised of a first material and at least one other plurality of filler particles comprised of a second material.

Also provided is a method of making the inventive medical devices wherein the method comprises selecting the nanoparticulate filler, selecting the matrix material, preparing a nanocomposite from the filler and matrix material, and preparing at least a component of the medical device from the nanocomposite material. Exemplary medical devices to which the invention is particularly directed include balloons, catheters, filters and stent delivery systems such as disclosed in U.S. Pat. Nos. 5,843,032; 5,156,594; 5,538,510; 4,762,129; 5,195,969; 5,797,877; 5,836,926; 5,534,007; 5,040,548; 5,350,395; 5,451,233; 5,749,888; 5,980,486; and 6,129,708, the full disclosures of each of which are hereby incorporated by reference herein for all purposes.

The inventive medical devices can have enhanced properties relative to, or properties absent from, a corresponding medical device not comprising a nanocomposite material. As a result, the inventive medical devices can provide certain advantages in their use. In this regard, the present invention also provides a method of treatment or diagnosis comprising bringing a medical device into therapeutic contact with a body to be treated or diagnosed, wherein the medical device comprises at least one nanocomposite material.

BRIEF DESCRIPTION OF THE DRAWINGS

The accompanying drawings, which are incorporated in and constitute a part of this application, illustrate several aspects of the invention and together with the description of the embodiments reserve to explain the principles of the invention. A brief description of the drawings is as follows:

FIG. 1 is a longitudinal cross-sectional view of the distal end of a medical device in accordance with the present invention;

FIG. 2 is a transverse cross-sectional view of the device shown in FIG. 1, taken at line 2-2; and FIG. 3 is a longitudinal cross-sectional view of the distal end of a medical device in accordance with the present invention.

DETAILED DESCRIPTION OF EMBODIMENTS OF THE INVENTION

The embodiments of the present invention described below are not intended to be exhaustive or to limit the invention to the particular embodiments disclosed in the following detailed description. Rather, the embodiments are described so that others skilled in the art understand the principles and practices of the present invention.

The present invention provides medical devices including at least one component comprised of at least one nanocomposite material. The invention can be particularly advantageous when applied to medical devices contemplated for either temporary or permanent treatment of the heart and/or circulatory system. For example, for treatment devices (such as an angioplasty catheter, angiography catheter, stent delivery system, etc.) the device desirably provides sufficient "pushability" that force applied at the proximal end is transmitted to the distal end to guide the distal end to the desired site. Such devices are also desirably "trackable" so that a positional movement, as to the right or the left, upward or downward, exerted by the operator at the proximal end translates to the desired motion at the distal end. Such devices are also desirably flexible enough so that when traversing a narrow and often tortuous space to get to the desired site, the device does not cause substantial injury to the surrounding tissue. Finally, it is often desired that the outer surface, or inner surface, of these devices be sufficiently lubricious so as to be easily passed over a guidewire and through the body to the desired site.

Devices intended to be used for a substantially permanent treatment have a corresponding number of desirable and yet diverse properties. For example, devices intended for implantation into the heart or vasculature to repair or replace certain parts thereof, such as artificial heart valves, artificial veins and arteries, or stents, desirably exhibit robust mechanical strength, and are yet flexible enough, to withstand the periodic yet continual contractual environment in which they must not only exist but function. The devices may also desirably be substantially nonthrombogenic due to the extended period of time these devices are contemplated to be resident within the body. Furthermore, in certain applications, such devices may desirably be biodegradable.

In order to achieve a combination of desired properties, more than one type of material is often employed in the construction of medical devices. For example, reinforcing filler particles can be added to a matrix material to form a composite material having a desired modulus, i.e., by acting as stress transmission elements and/or by concentrating or increasing the strain within the matrix material. Conventionally, the filler particles used in such composites are comprised of glass fibers, aggregates of amorphous or graphitic carbon, metal flakes, etc., and are at least about 1 micrometer in diameter in their largest dimension or larger. While such composite materials are useful in many medical device applications, the tolerances for many other medical device applications may not accommodate conventional, large size, filler particles.

Recently, a new class of filler particles has been described having at least one dimension less than about 1 micrometer. Filled polymer systems which contain such nanostructured particles have been termed nanocomposites. It has now been appreciated that these new materials can provide many unique advantages in the production of medical devices in accordance with the present invention. The use of nanocomposite materials in the manufacture of the inventive medical devices may provide the ability to control the modulus of a nanocomposite material while not affecting the processability thereof. Further, the use of nanocomposites may provide these advantages without substantially negatively impacting the compatibility between the nanocomposite and other materials that may be used in the manufacture of the medical device. Finally, by combining nanocomposites with other non-composite materials, it may be possible to control the directionality of change in the physical properties.

In addition to tailoring physical properties in small dimensions, nanocomposites may offer other significant advantages in medical device applications. For example, since in many cases the size of the nanofiller particle is smaller than the wavelength of visible light, it is possible to use nanocomposite materials to achieve the aforementioned advantages, while yet providing a transparent material. Such transparent nanocomposite materials could be useful, for example, to provide X-ray radiopaque materials that are optically clear. Other advantages unique to the use of nanocomposites in medical devices may include effects such as lowering the coefficient of friction, providing biocompatibility, and imparting biodegradability, to name a few.

Also, and without being limited to a particular theory, it is believed that because of the size of the nanoparticles, there is increased surface area contact between the filler particles and the matrix material in a nanocomposite as compared to a traditional filled polymer. This effect may be further enhanced by utilizing filler particles that are not only smaller than traditional filler particles, but also, that have high aspect ratios, i.e., a large ratio of their lateral dimension as compared to their thickness. Properties as good or better may thus be achieved in a nanocomposite as compared to the corresponding traditional filled polymer, while utilizing less filler material. Not only are performance and quality control significantly enhanced, cost savings can be seen that can be an important advantage in many medical device applications.

The term "nanocomposite", as used herein, generally refers to a composite material comprising a matrix material and a plurality of filler particles, wherein the filler particles are smaller than those utilized in conventional filled composites. More particularly, the term "nanocomposites" includes a matrix material comprising at least one plurality of filler particles having at least one dimension less than about 1000 nm in size. In some embodiments, the filler particles are between about 1 nm and 100 nm. Advantageously, nanocomposite materials can be engineered so that the nanocomposite exhibits the same properties as the matrix material to an enhanced degree and/or exhibits properties in addition to those exhibited by the matrix material alone. Utilizing nanocomposite materials in the manufacture of one or more components of medical devices may allow certain properties of the nanocomposites to be exploited in ways particularly advantageous in the medical device industry.

Any medical device can benefit from the application of the inventive concept of the present invention. As a result, the choice of the medical device in which to apply the concept is not particularly limited. It is believed, however, that the inventive concept will prove particularly advantageous when utilized in medical devices contemplated to be brought into therapeutic contact with a body, i.e., devices contemplated to be introduced into the body, either temporarily or permanently, for the purpose of effectuating a treatment or diagnosis thereof. Such devices find use in, e.g., urinary, cardiovascular, musculoskeletal, gastrointestinal, or pulmonary applications. Medical devices useful in urinary applications include, for example, catheters, shunts, stents, etc. Exemplary medical devices useful in cardiovascular applications include stents, angiography catheters, coronary or peripheral angioplasty catheters (including over the wire, single operator exchange or fixed wire catheters), balloons, guide wires and guide catheters, artificial vessels, artificial valves, filters, vascular closure systems, shunts, etc. Musculoskeletal medical devices include, for example, artificial ligaments and prosthetics. One example of a medical device useful in a gastrointestinal application would be a shunt. Pulmonary medical devices include prosthetics, as one example.

One example of a particular application in which the invention can be advantageously used is that of transluminal medical devices. Such devices include, e.g., catheters (e.g., guide catheters, angioplasty catheters, balloon catheters, angiography catheters, etc.) shunts, stents and stent delivery systems (e.g., self-expanding and balloon expandable), filters, etc. These devices often include extruded components made up of one, two, three, or more layers of materials. According to the invention, such devices include at least one nanocomposite material. That is, certain components of the device can include nanocomposite and non-nanocomposite materials. If multiple layers are used, at least one layer can be a nanocomposite material. The number and organization of the layers can be chosen to effectuate and/or to provide properties desired in the device. Further, in some embodiments, the quantity of filler particles of the nanocomposite material can vary at different regions of the nanocomposite. Such an alteration in the filler density can, for example, provide a device that has varying properties, such as flexibility, along its longitudinal axis.

In one exemplary embodiment, the medical device can be a catheter shaft such as for an angiography system, angioplasty balloon, guide catheter, or stent delivery system. Such devices often include multiple lumens in a side-by-side or coaxial configuration. Coaxial configurations generally have more than one lumen, wherein the lumens are typically fixed relative to one another and may be provided as coextruded single components, or may be separately extruded and then assembled by any conventional construction method to provide a multiple lumen structure. According to the invention, any of, or all of, the tubular components providing such a multiple lumen structure can be formed from a nanocomposite material. In some embodiments, the tubular component can be comprised of a plurality of layers wherein at least one layer of the tubular wall is a nanocomposite material. In such devices, the number and organization of the layers can be chosen to effectuate and/or provide the properties desired in the multilayer tubular component. Further, the dimensions of the device can be varied. For example, the layers of a multi-layered tubular wall can have a diverging or converging taper from the proximal end to the distal end of the wall.

As but one particular example of the embodiment of the invention wherein the medical device is a catheter shaft, conventionally reinforced with steel braiding, the catheter shafting may alternatively and advantageously be prepared utilizing a nanocomposite comprising, for example, ceramic nanofibers as the filler particles. Inasmuch as such a nanocomposite can be processed using normal extrusion processes, intermittent extrusion and/or multi-layer extrusion can be used to selectively include the ceramic nanofibers in order to further selectively stiffen areas of the shaft. Further advantageously, the ceramic nanofibers may be oriented, if desired, by employing rotating or counter-rotating extrusion, which orientation can provide enhanced torque performance of the shaft. If such orientation is not desired, ultrasonic vibrations can be introduced into the extrusion process in order to obtain a more randomized ceramic nanofiber orientation. In addition to these processing advantages, such shafting, while providing catheter shafting with a desired degree of reinforcement, would also be useful in MRI applications.

The nanocomposite material to be used in the present medical devices is not particularly restricted. Rather, any nanocomposite that can be engineered to display at least one of the properties desired in the desired medical device can be used. As is the case with the overall nanocomposite material, the material(s) that may be used as either the matrix material or the filler particle material is not restricted. Rather, nanocomposites to be utilized as disclosed herein can be comprised of any matrix material, or combinations thereof, and at least one plurality of filler particles.

The selection of the particular matrix material(s) and filler particle(s) for use in the nanocomposite(s) will depend on the intended use of the medical device into which the nanocomposite will be incorporated and desired properties of a device to be used in that manner. The matrix material and filler particle material(s) may then be chosen, e.g., to either enhance a property of the matrix material or to add a property otherwise absent from the matrix material so that selected properties are exhibited by the nanocomposite, which may not be exhibited by the matrix material alone. Such an enhancement or addition can provide the overall device with enhanced performance characteristics, or can provide greater quality control or enhanced tolerances in the manufacture of such devices.

Generally speaking then, the matrix material according to the invention may be any material suitable, or later determined to be suitable, for use in such a medical device. The matrix material may be any material that is historically or currently utilized, or contemplated for future use, in a corresponding medical device not comprising a nanocomposite component. The matrix material may be comprised of organic, inorganic or hybrid organic/inorganic materials. Additionally, the matrix material may be a single material or a combination of materials, e.g., the matrix material may be a metal alloy, copolymer or polymer blend.

Exemplary matrix materials include, for example, polymers, such as thermoplastics and thermosets. Examples of thermoplastics suitable for use as a matrix material include, for example, polyolefins, polyamides, such as nylon 12, nylon 11, nylon 6/12, nylon 6, and nylon 66, polyesters, polyethers, polyurethanes, polyureas, polyvinyls, polyacrylics, fluoropolymers, copolymers and block copolymers thereof, such as block copolymers of polyether and polyamide, e.g., Pebax®; and mixtures thereof. Representative examples of thermosets that may be utilized as a matrix material include elastomers such as EPDM, epichlorohydrin, nitrile butadiene elastomers, silicones, etc. Conventional thermosets such as epoxies, isocyanates, etc., can also be used. Biocompatible thermosets may also be used, and these include, for example, biodegradable polycaprolactone, poly(dimethylsiloxane) containing polyurethanes and ureas, and polysiloxanes.

Similarly, the filler particles may be comprised of any material suitable, or later determined to be suitable, for use in a medical device as a filler. Desirably, the filler particles comprise a material capable of at least minimally altering the physical, mechanical, chemical, or other properties of a matrix material when incorporated therein. The filler particles may comprise any material that has been historically used, is currently used, or is contemplated for use as a conventionally sized filler material in a medical device. Further, the filler particles may be comprised of organic, inorganic or hybrid organic/inorganic materials.

Exemplary filler particles include, among others, synthetic or natural phyllosilicates including clays and micas (that may optionally be intercalated and/or exfoliated) such as montmorillonite (mmt), hectorites, hydrotalcites, vermiculite, and laponite; monomeric silicates such as polyhedral oligomeric silsequioxanes (POSS) including various functionalized POSS and polymerized POSS; carbon and ceramic nanotubes, nanowires and nanofibers including single- and multi-walled fillerene nanotubes, silica nanogels, and alumina nanofibers; metal and metal oxide powders including aluminum oxide ($AlO_3$), titanium oxide ($TiO_2$), tungsten oxide, tantalum oxide, zirconium oxide, gold (Au), silver (Ag), platinum (Pt) and magnetic or paramagnetic powders such as neodinium iron boron, superparamagnetic ferrite oxide ($Fe_3O_4$) or superparamagnetic maghemite ($Fe_2O_3$); organic materials, including temperature sensitive polymers such as polyvinylpyrrolidone and n-isopropylacrylamide copolymers or blends, and poloxamer. Biodegradable polymers may also be used, may be magnetized, if desired, and include, for example, poly(lactic)acid, polysaccharide, and polyalkycyanoacrylate.

The present invention contemplates that there may be applications in which it will be desirable to have a combination of more than one plurality of filler particles, so that each different plurality may be comprised of a different material. In this manner, a further enhancement of a single desired property, or a new property broadening the array of properties, may be seen in the medical device prepared from such a nanocomposite. For example, it may be advantageous to prepare a nanocomposite from a polymeric matrix material, a first filler particle material that exhibits radio-opacity, and a second filler particle material that is influenced by magnetic fields. As a result, a medical device in accordance with the present invention may incorporate more than one plurality of nanoparticulate filler particles, wherein each plurality may comprise a different material.

As mentioned above, the filler particles used in the nanocomposites according to the invention can be comprised of any material utilized in a medical device as a conventionally sized filler. While such conventionally sized filler particles can range in size from several microns to several millimeters in size, the filler particles utilized in nanocomposites are desirably 1000 nm in the greatest dimension or less, more optimally, 750 nm or less, typically 500 nm or less, for example, from about 1 nm to about 100 nm. It is believed that the smaller the particle, the more easily dispersed within the matrix material it will be, and as a result, in embodiments where a uniform dispersion is desired, it is preferred that the particles are 100 nm or less in the greatest dimension.

Further, the filler particles, whatever material they are comprised of, may be of any shape, i.e., the filler particles can be generally spherical, octagonal or hexagonal, or they may be in the form of nanotubes, nanobelts, nanofibers, nanowires, etc. However, and as is mentioned above, the dispersion of the filler particles within the matrix material, as well as the interaction of the matrix material and the filler particles, may be enhanced by increasing the surface area contact between the matrix material and the filler particles, and as such, filler particles having a high aspect ratio, i.e., a large ratio of their lateral dimension to their thickness, may be particularly advantageous. For example, and whatever the geometry of the filler particle, it is contemplated that filler particles having aspect ratios of greater than 20:1 will be capable of promoting this increased dispersion and/or interaction between the filler particles and the matrix material. In some embodiments, the filler particles will desirably have aspect ratios of between 50:1 and 2500:1, typically between 200:1 and 2000:1, for example, from 300:1 to 1500:1.

The amount of the filler particles, or combinations of filler particles comprised of different materials, to be incorporated into the matrix can vary depending on the desired properties exhibited by a particular medical device or medical device component. Generally speaking, enough of the particles should be included so that desired properties are at least minimally exhibited by the nanocomposite, but not so much of the filler particles should be included so as to have a detrimental effect on the properties of the nanocomposite. While the particular range may vary depending on the filler particles and matrix material being utilized, nanocomposites exhibiting advantageous properties can be obtained by incorporating from about 0.005% to about 99% nanoparticles relative of the total final composition weight of the nanocomposite. In many embodiments, nanoparticles may be incorporated in an amount of from about 0.01% up to about 40% or 50% by weight of the nanocomposite. In a typical embodiment, the nanoparticles can be incorporated in an amount of from about 0.1% to about 20% of the nanocomposite, for example, from about 1% to about 10% by weight of the nanocomposite.

The properties of the nanocomposites may be affected by compatibility of, and/or the level and/or kind of interaction that occurs between, the filler particles and the matrix material of the nanocomposite. The compatibility of the filler particles and the matrix material may be minimal e.g., so that the interaction therebetween is limited to physical contact that occurs when the filler particles are simply dispersed within the matrix. Or, the compatibility may be such that the filler particles and the matrix interact physically, such as by chain entanglement of the filler particles with the matrix material. The filler particles and matrix material may also interact chemically, such as by the establishment of Van Der Waal's forces, covalent bonds or ionic bonds between the filler particles and the matrix material.

Generally speaking, any such compatibility, and the resulting interaction, can act to enhance the dispersion of the filler particles within the matrix material and/or to further enhance the properties of the nanocomposite as compared to a corresponding traditionally filled polymer. If this is the case, and very generally speaking, the greater the compatibility and more or stronger the interaction, the greater the increased dispersion and/or enhancement. Therefore, in applications where such greater dispersion or further property enhancement would be desirable, the compatibility of, and resulting interaction between, the filler particles with the matrix material can be encouraged or facilitated.

The compatibility of the filler particles and the matrix material can be enhanced, for example, simply by selection of the materials for use as the matrix or in the filler particles. That is, interaction between the filler particles and the matrix may be facilitated simply by selecting filler particles and matrix materials with compatible functional groups. If such compatible functional groups are not present, they can be provided by "functionalizing" the filler particles or matrix material to provide compatible functional groups that can then interact with each other. Phyllosilicates, monomeric silicates and ceramics are just a few examples of materials suitable for use in the filler particles that may be advantageously functionalized to provide increased interaction between the filler particles and the matrix material.

For example, POSS monomers can be functionalized with, e.g., organic side chains to enhance compatibility with, e.g., polystyrene. The ceramic boehmite (AlOOH) already has many surface available hydroxyl groups and, as such, may be further functionalized with, e.g., carboxylic acids, which in turn can be functionalized to interact with functional groups within the matrix material. Additionally, clays such as aluminosilicates or magnesiosilicates can be functionalized with block or graft copolymers wherein one component of the copolymer is compatible with the clay and another component of the copolymer is compatible with the polymer matrix. Or, clays such as montmorillonite may be functionalized with alkylammonium so that the clay is capable of interacting with a polyurethane, for example.

Advantageously, in those embodiments of the invention wherein the nanocomposite is desirably utilized in a multi-layered medical device, such as multi-layered tubing, and wherein at least two layers of the multi-layered device desirably comprise nanocomposite materials, functionalizers can be chosen for each layer that allow for the further optimization of the desirable properties of that layer, while potentially reducing compatibility issues between the layers. That is, in such embodiments of the invention, the at least two layers may comprise a nanocomposite material further comprising the same matrix material, or compatible matrix materials, and the same filler particles, but yet incorporating different functionalizers. The layers will thus be chemically compatible and easily coprocessed, and yet may exhibit different desirable properties.

In addition to functionalizing either or both the filler particles and/or matrix material, the compatibility of, and interaction between, the filler particles and matrix material can be enhanced by incorporating one or more coupling or compatibilizing agents into the nanocomposite to be used in the inventive medical devices. Whereas functionalizers, discussed above, generally increase compatibility by modifying either or both of the matrix material and filler particles to include compatible chemical groups in their respective structures, coupling or compatibilizing agents need not do so in order to effectuate such interaction. That is, suitable coupling/compatibilizing agents for use include any agent capable of enhancing compatibility and/or promoting interaction between the filler particles and the matrix without necessarily structurally modifying either or both the filler particles or matrix material. Such agents can be organic or inorganic.

The selection of these optional agents will, of course, depend on the matrix and filler particle materials selected. Bearing this in mind, suitable organic coupling agents can be both low molecular weight molecules and polymers. Examples of low molecular weight organic coupling/compatibilizing agents include, but are not limited to, amino acids and thiols. For example, 12-aminododecanoic acid may be used to compatibilize clay within any desired thermoplastic matrix. Examples of polymeric compatibilizers include functionalized polymers, such as maleic anhydride containing polyolefins or maleimide-functionalized polyamides. One example of a nanocomposite wherein the compatibility may be enhanced via the inclusion of such a polymeric compatibilizer would be a polyolefin or nylon 12/montmorillonite nanocomposite, which may further include an amount of maleic anhydride functionalized polypropylene to compatibilize the matrix material and filler particles. Inorganic coupling agents would include, for example, alkoxides of silicon, aluminum, titanium, and zirconium, to name a few.

Generally speaking, the amount of a coupling/compatibilizing agent used, if used at all, will desirably be that amount which will at least marginally improve the compatibility of the filler particles and the matrix material so that at least a minimal enhancement of the dispersion of the filler particles within the matrix and/or the properties of the nanocomposite can be observed. Useful amounts of such agents are contemplated to be within the ranges of from about 0.01% to about 10% by weight of the nanocomposite; typically from about 0.05% to about 5.0%, more typically from about 0.1% to about 1% by weight of the nanocomposite.

In addition to material selection, functionalizing and/or the use of compatibilizing agents as a means to promote interaction of the filler particles throughout the matrix material, the dispersion of the filler particles may be enhanced, if desired, by utilizing ultrasonic assisted extrusion and/or compounding. That is, by applying an ultrasonic vibration to the extruder die, the friction shear forces can be reduced and the melt rendered more homogeneous. More particularly, such an extruder could include, e.g., an extruder head capable of extruding a polymer melt having an ultrasonic transducer operatively disposed thereto. The ultrasonic transducer would be capable of transmitting ultrasonic waves to the extruder head, which waves may further advantageously be modulated to include at least one amplitude and modulation. In this manner, the waves provided to the extruder head may, if desired, be provided as substantially uniform vibrations to substantially the entirety of the extruder head.

An additional method for enhancing the dispersion of the filler particles throughout the matrix material could include dispersing the filler particles in a solvent, e.g., dimethylformamide, dichloroethylene, N-methyl-2-pyrrolidone, and the like. Once so dispersed, the filler particles could be mixed with a similarly dissolved matrix material and sprayed onto a mandrel to produce a nanocomposite material with enhanced dispersion of the filler particles. Any other known techniques of enhancing the dispersion of filler particles within a matrix can also be utilized, if such an enhanced dispersion is desirable in the chosen application.

If dispersion of the matrix material and/or filler particles within a solvent is desired, either or both of the matrix material or filler particles may be functionalized in order to effectuate their dispersability within a desired solvent. That is, in addition to functionalizing either or both of the matrix material and/or filler particles so that they are more compatible with one another once formed into a nanocomposite material, either or both of the matrix material and/or filler particles may be functionalized to effectuate their dispersability within a solvent, in order to further enhance the dispersability of the filler particles within the matrix material. As but one example of this embodiment of the present invention, single-walled carbon nanotubes may be functionalized with, e.g., carboxylic acid groups that are then subsequently converted to acyl chloride, followed by conversion to an amide, to render the nanotubes dispersable in organic solutions. As an additional example, functionalization with mono-amine terminated poly(ethylene oxide) or glucosamine can render single walled carbon nanotubes soluble in aqueous solutions. Such functionalization of nanotubes to enhance their dispersion within aqueous or organic solvents is described in, e.g., U.S. Pat. Nos. 6,331,262 and 6,368,569, as well as Pompeo and Resasco, "Water Solubilization of Single Walled Carbon Nanotubes by Functionalization with Glucosamine" Nano Letters, 2(4), pp 369-373 (2002) and Bandyopadhyaya et al., "Stabilization of Individual Carbon Nanotubes in Aqueous Solutions", Nano Letters, 2(1), pp 25-28 (2002), the entire disclosures of each being hereby incorporated by reference herein.

While it may be desirable in certain applications to increase the interaction between the nanoparticles and the matrix material, or between the nanoparticles and the device itself, extensive interaction between the nanoparticles themselves can be undesirable in certain applications. In particular, in applications where the nanoparticles desirably form a layer with a substantially uniform thickness, or where an otherwise substantially uniform dispersion throughout a matrix material or relative to a medical device is desired, any substantial agglomeration of the nanoparticles can be suboptimal. In such applications then, it may be advantageous or desirable to include a dispersant in solution with the nanoparticles prior to their dispersion within, or application to, the matrix material and/or the inventive device.

As but one example of this aspect of the invention, and in that embodiment wherein the nanoparticles desirably comprise carbon nanoparticles, such as carbon nanotubes, natural carbohydrates may be utilized to minimize or eliminate the interactions between the carbon nanotubes that may otherwise occur when the nanotubes are desirably solubilized. See, e.g., Dagani, "Sugary Ways to Make Nanotubes Dissolve", Chemical and Engineering News, 80(28), pages 38-39; and Star et al., "Starched carbon nanotubes" Angewandte Chemie-International Edition, 41(14), pp. 2508 (2002), the entire disclosures of which are incorporated by reference herein.

In particular, in order to provide a solution of substantially non-aggregated carbon nanotubes that may then be mixed with a similarly dispersed matrix material or simply applied to a matrix material by spraying or dipping, the carbon nanotubes may be dispersed in an aqueous solution comprising such a natural carbohydrate. Illustrative examples of such natural carbohydrates include, but are not limited to, starches; gums, e.g., gum arabic, and sugars gum. This solution can then be dried to form a substantially non-aggregated powder of carbon nanotubes and gum arabic that may then be compounded with a matrix material and processed into the desired medical device according to conventional techniques, or the solution may be used to create uniform layers of substantially non-aggregated carbon nanotube fibers on the surface of a matrix material, on the surface of a component of a medical device, or onto substantially the totality of a surface of a medical device in order to provide a medical device in accordance with the present invention. If a uniform layer is desired, once the carbon nanotube/gum arabic solution has been prepared, the desired material may simply be coated with the solution by dipping the material in the solution and allowing the water to evaporate, leaving behind a substantially uniform layer of substantially non-aggregated carbon nanotubes. As discussed hereinabove, if desired, the carbon nanotubes can advantageously be functionalized prior to any such dispersion.

Such a layer of carbon nanotubes may be used as a tie layer between polymer layers of a medical device, e.g., by depositing the carbon nanotubes as described on at least one of the surfaces to be thermally bonded. Upon thermal bonding of the two layers, the interspersed tie layer of carbon nanotubes would provide additional reinforcement to the bond site. This advantageous technology may be applied to embodiments where a tie layer is desired between two layers of material wherein the second layer of material is applied to the first via welding, spraying, or multilayer extrusion and/or wherein electrical conductivity is desired. In such embodiments, the carbon nanotube/gum arabic solution would simply be applied to the first material and allowed to dry, and the second material subsequently applied according to the desired technology over the substantially uniform carbon nanotube layer. Further, the physical interaction between the carbon nanotubes and the matrix material can be supplemented by functionalizing the arabic gum with functionalizers as described above, providing a further opportunity to reinforce the bond site.

In addition to the filler particles, the matrix material and, optionally, a coupling/compatibilizing agent, the nanocomposites according to the invention can comprise any other materials utilized in a corresponding medical device not comprising a nanocomposite. For example, pigments and/or whiteners, and/or conductive, magnetic and/or radiopaque agents could be provided in the nanocomposites, if desired. Also processing aids, such as plasticizers, surfactants and stabilizers, can be included in the nanocomposites. Such agents, the amounts in which they are useful, as well as the benefits that they provide, are well known to those of ordinary skill in the art.

One example of a class of stabilizers that may find use in the inventive medical devices and methods is that commonly referred to as radiation oxidative degradations, or "ROD" stabilizers. As the name suggests, these agents may assist a polymer within which they are incorporated to resist any degradation that may otherwise occur upon exposure of the polymer to sterilizing radiation. Additionally, however, such stabilizers may also be useful in assisting a polymer to resist any degradation that may otherwise occur during processing, such as during mixing and/or heating that may be required in order to adequately disperse nanoparticles throughout a matrix material.

Such ROD stabilizers may be antioxidants, particularly radical or oxygen scavengers. Mercapto compounds, hindered phenols, phosphites, phosphonites and hindered amine antioxidants are among the most effective such stabilizers. Specific examples of stabilizers are 2-mercaptobenzimidazole, trilauryl phosphite, IONOX 330, 2-mercaptobenzothiazole, N,N-di(β-napthyl-p-phenylenediamine) (DPPD), SANTONOX R, SANTOWHITE powder, phenothiazine, IONOL, 2,6-di-t-butylcresol, N-cyclohexyl-N'-phenyl-p-phenylenediamine, nickel dibutyldithiocarbamate, IRGANOX 1010, β-(3,5-di-t-butyl-6-hydroxyphenyl) propionate, 1,2,2,6,6-pentamethyl-4-stearoyl piperidine, and 2,2,6,6, tetramethyl-4-nitropiperidine. Further examples include butylated reaction product of p-cresol and dicyclopentadiene, substituted amine oligomers, N,N'-bis(2,2,6,6-tetramethyl-4-piperidinyl)-1,6-hexanediamine, 2,4-dichloro-6-(4-morpholinyl)-1,3,5-triazine, and N,N'-hexamethylene-bis[3-(3,5-di-t-butyl-4-hydroxyphenyl)propionamide]. Still further, transition metals or compounds thereof may function as ROD stabilizers, for instance iron, cobalt, nickel, ruthenium, rhodium, palladium, osmium, iridium, platinum, copper, manganese and zinc metal and compounds, as described in International Pub. No. WO 99/38914, U.S. Pat. No. 5,034,252 and U.S. Pat. No. 5,021,515.

The ROD stabilizer may also be an oxygen scavenging polymer, such as the polyketone polymers described in International Pub. No. WO 96/18686 of the formula

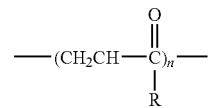

where R is H, an organic side chain or a silicon side chain, and n is a positive number greater than 2. Such polyketone ROD stabilizers are suitably employed in the thermoplastic composition in an amount of from 0.1 to about 10% by weight.

If their presence is desired, ROD stabilizers may be employed in the nanocomposites in any amount at least minimally effective in assisting in the resistance of the matrix material to degradation, i.e., in amounts of from about 0.01% to about 5%, suitably from about 0.1 to about 1%, for instance from 0.2% to 0.5%. The stabilizer can be compounded into the nanocomposite in the extrusion melt or in a separate compounding step prior thereto.

Many nanocomposites and nanoparticles are commercially available. Additionally, many methods of producing nanocomposites and/or nanoparticles are known, and any of these can be utilized to produce nanocomposites and nanoparticles for incorporation into the inventive medical device. Many such methods are disclosed and described, for example, in "Nanocomposites 2001, Delivering New Value to Plastics", Executive Conference Management, Jun. 25-27, 2001, Chicago, Ill., the entire disclosure of which is incorporated by reference herein.

Advantageously, and since the filler particles can have an impact on the properties exhibited by the nanocomposite by virtue of the dispersion of the filler particles within the matrix, the particular method utilized to prepare the nanocomposite can be selected to assist in the provision of a medical device with the desired array of properties. That is, in certain medical device applications, it may be desirable to have the entirety of the medical device or medical device component exhibit the properties of the nanocomposite substantially uniformly throughout, or across the length of, the medical device. In such applications, it would be desirable to substantially uniformly distribute the filler particles throughout the matrix of the nanocomposite. In other applications, it may be desirable to have the entirety of the medical device or medical device component exhibit the properties of the nanocomposite, but at varying degrees throughout the device or component. In these applications, then, it would be desirable to vary the distribution of the filler particles throughout the matrix of the nanocomposite in a manner so that the desired varied properties are observed in the medical device or component.

For exemplary purposes only, then, processes for the production of such nanocomposites include polymerization of the matrix material in the presence of the filler particles, melt compounding of the matrix material with the filler particles, and in-situ formation of the filler particles, e.g., as would be provided by the adding a silane monomer to a block copolymer and then curing the silane to produce nanostructured silica filler particles relatively uniformly dispersed within the matrix material of the copolymer, to name a few. If a coupling/compatibilizing agent is to be used, it may be precoated onto the filler particles before compounding the filler particles with the matrix, or alternatively, the agents may be added during the nanocomposite formation process.

Generally, one of the advantages of the utilization of nanocomposites is that, at least as compared to traditionally filled polymers, nanocomposites are often more easily processed. As a result, once the nanocomposite has been prepared, it can be processed into the desired medical device by any method known to those of ordinary skill in the art, and the particular method chosen is not critical to the practice of the present invention. There are a multiplicity of methods for the manufacture of medical devices that are thus appropriate, examples of which include, but are not limited to, foam processing, blow molding or film molding, sheet forming processes, profile extrusion, rotational molding, compression molding, thermoset pre-preg processes and reaction injection molding processes. Of course, the inventive medical device can be manufactured by any method utilized to manufacture a corresponding medical device not comprising a nanocomposite.

The invention will now be further illustrated in the following examples, which are not intended to be limiting, but rather have been chosen and described so that others skilled in the art may appreciate and understand the principles and practices of the present invention.

Example 1

Preparation of Inner Shaft Catheter Tubing with an HDPE/POSS Nanocomposite

1) Preparation of the HDPE/POSS Nanocomposite by Twin-Screw Extrusion Compounding An organically functionalized POSS (MS0830, an OctaMethyl-POSS commercially available from Hybrid Plastics, Fountain Valley, Calif.) was compounded with high density polyethylene (HDPE Marlex 4903, commercially available from Chevron-Phillips Chemical Company, Houston, Tex.). In particular, a material feed ratio of HDPE to POSS of 4:1 was fed into a counter rotating dispersive twin screw compounder ZSSE 27 (commercially available from Leistritz Company, Allendale, N.J.) operating at 190° C. and a speed of 200 RPM. The compounding output was at 5 pounds per hour.

2) Extrusion of Inner Shaft Catheter Tubing Incorporating HDPE/POSS Nanocomposite Material A 4:1 mixture of the HOPE/POSS nanocomposite to Plexar 390 anhydride modified polyethylene (commercially available from Equistar Chemical Company, Houston, Tex.) was premixed and then further diluted at a 3:1 ratio with Marlex 4903 polyethylene and extruded into tubing of dimensions of 0.018 inch×0.024 inch at 220° C. The resulting inner shaft tubing could be used in an over the wire, single operator exchange catheter, or stent delivery system using conventional construction techniques.

Example 2

Preparation of Outer Shaft Catheter Tubing with a Pebax®/POSS Nanocomposite

1) Preparation of the Pebax®/POSS Nanocomposite by Twin-Screw Extrusion Compounding An organically functionalized POSS (AM0265, an Aminopropylisobutyl-POSS commercially available from Hybrid Plastics) was compounded with Pebax®7233 (Pebax® is a polyether block amide commercially available from Atofina, Brussels, Belgium). In particular, a material feed ratio of Pebax® to POSS of 4:1 was fed into a counter rotating dispersive Leistritz ZSE 27 twin screw compounder operating at 200° C. and a speed of 100 RPM. The compounding output was at 5 pounds per hour.

2) Extrusion of Outer Shaft Catheter Tubing Incorporating Pebax®/POSS Nanocomposite Material A 3:1 dilution of the Pebax®/POSS nanocomposite to Pebax®7233 was prepared and extruded into outer shaft tubing with dimensions of 0.0306 inch×0.0362 inch at 226° C.

During the tubing extrusion process, the nanocomposite may be more stable than conventional filled Pebax®. If the tubing produced by this method were subject to an EtO sterilization, that the POSS nanofiller will reduce or substantially prevent the oriented Pebax® chains from relaxing to a detrimental degree, as compared to such relaxation that would be expected to occur in an unfilled Pebax® medical device or device component when subjected to such sterilizing treatment.

Example 3

Preparation of Outer Shaft Catheter Tubing with a Pebax®/Clay Nanocomposite

A Pebax®/clay nanocomposite material said to contain 95% Pebax® 7233 and 5% clay filler with the trade designation of 2099×83109 C was purchased from RTP Company (Winona, Minn.). The material was extruded into acceptable outer shaft tubing with dimensions of 0.0306 inch×0.0362 inch at an extrusion temperature of 226° C.

Example 4

Preparation of Multilayer Tubing with a Pebax®/Montmorillonite Nanocomposite

A Pebax®/montmorillonite nanocomposite material containing 95% of a 72 durometer Pebax® material (such as Pebax® 7233 commercially available from Atochem) and 5% montmorillonite filler will be compounded with a twin screw extruder as described above. The nanocomposite material will then be coextruded with non-filled Pebax® at a temperature sufficient to provide appropriate viscosity for extrusion, i.e., from about 190° C. to about 215° C., into acceptable trilayer tubing having the Pebax®/montmorillonite nanocomposite as a middle layer and non-filled Pebax® as the inner and outer layers. The trilayer tubing will have dimensions appropriate for the intended use of the tubing. If the tubing is to be used, e.g., in the formation of a balloon, suitable dimensions would be an inner diameter of about 0.0176 inch and an outer diameter of about 0.342 inch.

Example 5

Preparation of Monolayer Tubing with a Pebax®/Modified Montmorillonite Nanocomposite A Pebax®/montmorillonite nanocomposite material containing 90% of a 70 durometer Pebax® material (such as Pebax® 7033 commercially available from Atochem) and 10% modified montmorillonite filler will be compounded with a twin screw extruder as described above. Prior to compounding, the montmorillonite will be modified with a functionalizer comprising a block copolymer capable of interacting with polyether and/or polyamide, as described hereinabove. The nanocomposite material will be extruded at a temperature sufficient to provide appropriate viscosity for extrusion, i.e., from about 190° C. to about 215° C., into acceptable monolayer tubing having dimensions appropriate for the intended use of the tubing. This tubing can then be used to form balloons, the inner lumen of catheters, the outer lumen of catheters, and the like. If the tubing is to be used, e.g., in the formation of a balloon, suitable dimensions would be an inner diameter of about 0.0176 inch and an outer diameter of about 0.342 inch.

Example 6

Preparation of Monolayer Tubing with a Nylon 12/Modified Montmorillonite Nanocomposite A nylon 12/montmorillonite nanocomposite material containing 99% of a nylon 12 (commercially available under the trade name Rilsan® from Atofina) and 1% modified montmorillonite filler will be prepared as follows. All materials will either be purchased as powders or ground into powders by any known method. The montmorillonite will be modified with a functionalizer comprising block polyamide or any material having polyamide groups, as described hereinabove. The powdered nylon 12 and powdered functionalized montmorillonite will be mixed together and fed into an extrusion process via a gravimetric feeding device (or any other acceptable powder feeding mechanism). The nanocomposite material will then be extruded at a temperature sufficient to provide appropriate viscosity for extrusion, i.e., from about 210° C. to about 240° C., typically 220° C. to 230° C., into acceptable monolayer tubing having dimensions appropriate for the intended use of the tubing. Such uses could include, e.g., formation of balloons, inner lumens of catheters, outer lumens of catheters, etc. Tubing comprising such a nanocomposite is contemplated to be particularly useful in the formation of balloons, for which use appropriate tubing dimensions are an inner diameter of about 0.0176 inch and an outer diameter of about 0.342 inch. More particularly, the balloon could be formed by any known method and subsequently attached to catheter shafting by any known construction method.

Example 7

Preparation of Heat Bonded Multilayer Catheter Shafting Comprising a Single Walled Carbon Nanotube Tie Layer Multilayer catheter shafting will be prepared comprising a layer of Pebax® and a layer of Plexar® (anhydride modified polyethylene commercially available from Equistar Chemical Company, Houston, Tex.), having a tie layer of single walled carbon nanotubes therebetween using an over-the-wire tandem extrusion process as follows:

Plexar® will be extruded onto a Teflon coated copper mandrel at 220° C. An aqueous solution of arabic gum and single wall carbon nanotubes (1 ml purified water, 200 mg gum arabic, 30 mg carbon nanotubes) will then be sprayed onto the Plexar® shafting. Any excess water will be removed by running the shafting through a 120° C. oven. A second extruder in tandem will extrude a layer of Pebax® over the Plexar carbon nanotubes at a temperature of 226° C. The resulting multilayer tubing will exhibit enhanced bond strength between the layers due to the embedment of the carbon nanotubes at the interface layer.

Example 8

Effect of Different Functionalizers on Performance and Properties of Pebax®/Clay Nanocomposites Three nanocomposites were prepared comprising 95% Pebax® 7233 and 5% clay. More particularly, a first such nanocomposite comprising unmodified clay, a second such nanocomposite comprising clay modified with a block copolymer having hydroxyl end groups and a third such nanocomposite comprising clay modified with a block copolymer having carboxylic end groups were separately compounded with a twin screw extruder as described above. The material was extruded into tubing and tested on an Instron. The elongation at break (epsilon), elasticity modulus (E) as well as the ultimate strength (sigma) were measured. The results are provided below in Table 1:

TABLE 1

| | E(N/mm$^2$) | Sigma (N) | Epsilon % |
|---|---|---|---|
| Unmodified clay/Pebax ® nanocomposite | 576.7 | 41.0666 | 128.94 |
| ROH modified clay/Pebax ® nanocomposite | 669.3 | 42.96667 | 200.8667 |
| RCOOH modified clay/Pebax ® nanocomposite | 650.1 | 44.225 | 152.755 |

As is shown, the properties of the modified clay nanocomposites vary significantly. In order to take advantage of this variation, for example, the ROH modified clay/Pebax® nanocomposite could be used as an outer layer for a balloon, thereby obtaining an increase of approximately greater than 50%, typically greater than 40%, for example greater than 25%, in puncture resistance due to the increase in epsilon. If the RCOOH modified clay/Pebax® nanocomposite were then utilized as an inner layer of the same balloon, the burst resistance could be increased as a result of the measured increase in overall strength that was seen in this nanocomposite relative to a nanocomposite comprising an unmodified clay.

Referring now to FIGS. 1 and 2, there is illustrated an embodiment of a medical device according to the invention.

In particular, FIG. 1 is a longitudinal cross-sectional view of the distal end of a balloon angioplasty catheter 10. In this embodiment, catheter 10 includes an inner tubular component 1 comprising an inner layer 2 and outer layer 3. A balloon 4 having a distal waist 5 is attached to inner tubular component 1. Balloon 4 also has a proximal waist 6 attached to outer tubular component 7. A guidewire 11 is shown within lumen 12 of inner tubular member 1. FIG. 2 is a transverse cross-sectional view taken at line 2-2 of FIG. 1.

According to the invention, it will be appreciated that inner tubular component 1, inner layer 2, outer layer 3, balloon 4, or outer tubular component 7, or guidewire 11, can be prepared in whole or in part from a nanocomposite material as disclosed herein. In addition, any of these components can be a single layer or a multiple layer with one or more of the layers comprising a nanocomposite. Thus, for example, in FIGS. 1 and 2, inner tubular component 1 is illustrated with multiple layers wherein, either or both of layers 2 and 3 of inner tubular component 1 can be prepared from a nanocomposite material. Thus, for example, either of layers 2 or 3 can comprise a nanocomposite material prepared as described in Examples 1-3 above. In other embodiments, referring to FIG. 3, inner tubular component 1 includes two nanocomposite layers 15, 15' and a normanocomposite layer 17 between the nanocomposite layers. As shown, nanocomposite layer 15 and normanocomposite layer 17 are tapered, and balloon 4 includes two layers 19, 21. Either or both of layers 19, 21 can be prepared from a nanocomposite material, as indicated above.

Also as disclosed earlier, a stent delivery system including the stent mounted over balloon 4 can be prepared according to the invention. In addition, components known in the art for use with balloon expandable stent delivery systems, such as sleeves, disclosed for example in U.S. Pat. No. 4,950,227 can be used. Based on this disclosure, it will be appreciated that self-expanding stent delivery systems, guide catheters, angiography catheters, etc., can also be prepared within the scope of the invention.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. An intravascular balloon catheter comprising:
an outer tubular member;
an inner tubular member disposed coaxially within the outer tubular member, the inner tubular member defining a guidewire lumen; and
an inflatable balloon having a proximal waist and a distal waist, wherein the balloon is attached to the outer tubular member at the proximal waist and the balloon is attached to the inner tubular member at the distal waist;
wherein at least a portion of the outer tubular member comprises a nanocomposite material;
wherein the nanocomposite material comprises a matrix material and at least one plurality of nanoparticles;
wherein the plurality of nanoparticles comprise a clay;
wherein the plurality of nanoparticles has a varying quantity along a longitudinal axis of the outer tubular member; so as to vary a flexibility of the outer tubular member.

2. An intravascular balloon catheter comprising:
an outer tubular member;
an inner tubular member having at least an inner layer and an outer layer, the inner tubular member disposed coaxially within the outer tubular member; and
an inflatable balloon having a proximal waist and a distal waist, wherein the balloon is attached proximate the distal end of the outer tubular member at the proximal waist and the balloon is attached proximate the distal end of the inner tubular member at the distal waist;
wherein at least a portion of the outer tubular member comprises a first nanocomposite material that includes a thermoplastic matrix material or a thermoset matrix material, and further includes at least a first plurality of nanoparticles having a varying quantity along a longitudinal axis of the outer tubular member so as to vary a flexibility of the outer tubular member.

3. The balloon catheter of claim 2, wherein the nanoparticles in the first plurality comprise a clay.

4. The balloon catheter of claim 3, wherein the clay comprises montmorillonite.

5. The balloon catheter of claim 2, wherein at least one of the inner layer and the outer layer of the inner tubular member comprises a second nanocomposite material.

6. The balloon catheter of claim 2, wherein a portion of the outer tubular member comprises a material other than a second nanocomposite material.

7. The balloon catheter of claim 2, wherein a portion of the outer tubular member comprises a material other than a first nanocomposite material.

8. The balloon catheter of claim 2, wherein the nanoparticles in the first plurality comprise carbon nanotubes, ceramic nanotubes, carbon fibers or ceramic fibers.

9. The balloon catheter of claim 2, wherein the first nanocomposite material further includes a second plurality of nanoparticles.

10. The balloon catheter of claim 2, wherein the first nanocomposite material further comprises a functionalizer.

11. The balloon catheter of claim 10, wherein the functionalizer is an alkylammonium.

12. An intravascular balloon catheter comprising:
an outer tubular member;
an inner tubular member having an inner layer and an outer layer, the inner tubular member disposed coaxially within the outer tubular member; and
an inflatable balloon having a proximal waist and a distal waist, wherein the balloon is attached to the outer tubular member at the proximal waist and the balloon is attached to the inner tubular member at the distal waist;
wherein at least a portion of the outer tubular member is comprised of a nanocomposite material, the nanocomposite material including a matrix material comprised of nylon 12, at least one plurality of nanoparticles comprised of a clay, and a functionalizer;
wherein the at least one plurality of nanoparticles has a varying quantity along a longitudinal axis of the outer tubular member so as to vary a flexibility of the outer tubular member.

* * * * *